(12) United States Patent
Lee et al.

(10) Patent No.: US 12,221,426 B2
(45) Date of Patent: Feb. 11, 2025

(54) INHIBITORY MATERIAL AGAINST HUMAN BODY-DERIVED NICOTINAMIDE ADENINE DINUCLEOTIDE PHOSPHATE-DEPENDENT STEROID DEHYDROGENASE-LIKE, AND ANTICANCER AGENT COMPRISING SAME AS EFFECTIVE INGREDIENT OR PHARMACEUTICAL COMPOSITION COMPRISING SAME AS EFFECTIVE INGREDIENT FOR TREATMENT OF HYPERLIPIDEMIA

(71) Applicants: SEOUL NATIONAL UNIVERSITY R&DB FOUNDATION, Seoul (KR); KOREA RESEARCH INSTITUTE OF CHEMICAL TECHNOLOGY, Daejeon (KR); NATIONAL CANCER CENTER, Gyeonggi-do (KR)

(72) Inventors: Bong-Jin Lee, Seoul (KR); Kyu-Yeon Lee, Seoul (KR); Sang Jae Lee, Seoul (KR); Dong-Gyun Kim, Seoul (KR); Joo Youn Lee, Daejeon (KR); Kwan-Young Jeong, Daejeon (KR); Heui Cherl Yang, Daejeon (KR); Hyeon-Kyu Lee, Daejeon (KR); Hyoun Sook Kim, Gyeonggi-do (KR)

(73) Assignees: Seoul National University R&DBFoundation, Seoul (KR); Korea Research Institute of Chemical Technology, Daejeon (KR); National Cancer Center, Gyeonggi-do (KR)

( * ) Notice: Subject to any disclaimer, the term of this patent is extended or adjusted under 35 U.S.C. 154(b) by 935 days.

(21) Appl. No.: 17/271,354

(22) PCT Filed: Aug. 29, 2019

(86) PCT No.: PCT/KR2019/011094
§ 371 (c)(1),
(2) Date: Feb. 25, 2021

(87) PCT Pub. No.: WO2020/046020
PCT Pub. Date: Mar. 5, 2020

(65) Prior Publication Data
US 2021/0253544 A1 Aug. 19, 2021

(30) Foreign Application Priority Data

Aug. 30, 2018 (KR) .................. 10-2018-0103008
Aug. 27, 2019 (KR) .................. 10-2019-0105425

(51) Int. Cl.
*C07D 277/32* (2006.01)
*A61P 3/06* (2006.01)
(Continued)

(52) U.S. Cl.
CPC .............. *C07D 277/32* (2013.01); *A61P 3/06* (2018.01); *A61P 35/00* (2018.01)

(58) Field of Classification Search
CPC .......... C07D 277/32; A61P 3/06; A61P 35/00; A61K 31/426
See application file for complete search history.

(56) References Cited

U.S. PATENT DOCUMENTS

| | | | |
|---|---|---|---|
| 2010/0016292 A1* | 1/2010 | Pellecchia | C07D 491/04 514/236.5 |
| 2019/0307729 A1* | 10/2019 | Kao | C11D 3/48 |

FOREIGN PATENT DOCUMENTS

| | | |
|---|---|---|
| WO | 94/29287 | 12/1994 |
| WO | 2011/135303 | 11/2011 |

(Continued)

OTHER PUBLICATIONS

Ross R, Harker L. Hyperlipidemia and atherosclerosis. Science. Sep. 17, 1976;193(4258):1094-100. doi: 10.1126/science.822515. PMID: 822515. (Year: 1976).*

(Continued)

*Primary Examiner* — Bruck Kifle
*Assistant Examiner* — Kevin S Martin
(74) *Attorney, Agent, or Firm* — Licata & Tyrell P.C.

(57) ABSTRACT

A nicotinamide adenine dinucleotide phosphate-dependent steroid dehydrogenase-like (NSDHL) inhibitor provided according to an aspect of the present invention can be used not only as an anticancer agent capable of overcoming resistance to EGFR-targeting anticancer agents, but also advantageously in the treatment of hyperlipidemia.

2 Claims, 2 Drawing Sheets

(51) Int. Cl.
*A61P 35/00* (2006.01)
*A61K 31/426* (2006.01)

(56) References Cited

FOREIGN PATENT DOCUMENTS

| WO | WO-2011135303 A2 * | 11/2011 | ............. A61K 31/34 |
| WO | 2017/215552 | 12/2017 | |
| WO | WO-2017215552 A1 * | 12/2017 | ............. A01N 43/78 |

OTHER PUBLICATIONS

National Cancer Institute, Chemotherapy, 2024 (Year: 2024).*
Yoon SH et al. Abstract 1800: Novel NSDHL inhibitor (Compound 9) exerts anti-proliferative and cytotoxic activity in breast cancer cells, Cancer Research, 2022, vol. 22 (Year: 2022).*
Helliwell SB et al. FR171456 is a specific inhibitor of mammalian NSDHL and yeast Erg26p. Nat Commun. Oct. 12, 2015;6:8613. doi: 10.1038/ncomms9613. PMID: 26456460; PMCID: PMC4633953. (Year: 2015).*
NIH National Library of Medicine, STATPearls, Hyperlipidemia, 2023 (Year: 2023).*
Gleeson MP, Hersey A, Montanari D, Overington J. Probing the links between in vitro potency, ADMET and physicochemical parameters. Nat Rev Drug Discov. Mar. 2011; 10(3):197-208. doi: 10.1038/nrd3367. PMID: 21358739; PMCID: PMC6317702. (Year: 2011).*
Dictionary.com, in vitro, 2024, https://www.dictionary.com/browse/in-vitro (Year: 2024).*
Pauling, General Chemistry, CH 7, The Nonmetallic Elements and Some of Their Compounds, 2014, p. 217 (Year: 2014).*
International Search Report in PCT/KR2019/011094 dated Dec. 2, 2019.
Johnson et al. "Rhodanine Derivatives as Selective Protease Inhibitors Against Bacterial Toxins" Chem Biol. Drug Design 2008 71:131-139.
Sun et al. "Discovery of 1, 3-dipehnyl-1H-pyrazole derivatives containing rhodanine-3-alkanoic acid groups as potential PTP1B inhibitors" Bioorganic & Medicinal Chemistry Letters 2019 29:1187-1193.
Insuasty et al. "Synthesis, Antifungal and Antitumor Activity of Novel (Z)-5-Hetarylmethylidene-1, 3-thiazol-4-ones and (Z) -5-Ethylidene-1, 3-thiazol-4-ones" Molecules 2013 18:5482-5497.

* cited by examiner

INHIBITORY MATERIAL AGAINST HUMAN BODY-DERIVED NICOTINAMIDE ADENINE DINUCLEOTIDE PHOSPHATE-DEPENDENT STEROID DEHYDROGENASE-LIKE, AND ANTICANCER AGENT COMPRISING SAME AS EFFECTIVE INGREDIENT OR PHARMACEUTICAL COMPOSITION COMPRISING SAME AS EFFECTIVE INGREDIENT FOR TREATMENT OF HYPERLIPIDEMIA

This patent application is the National Stage of International Application No. PCT/KR2019/011094 filed Aug. 29, 2019, which claims the benefit of priority from Korean Application No. 10-2018-0103008, filed Aug. 30, 2018, and Korean Application No. 10-2019-0105425 filed Aug. 27, 2019, teachings of each of which are herein incorporated by reference in their entirety.

BACKGROUND OF THE INVENTION

1. Field of the Invention

The present invention relates to an inhibitory material against human-derived nicotinamide adenine dinucleotide phosphate-dependent steroid dehydrogenase, and an anti-cancer agent or a pharmaceutical composition for treating hyperlipidemia comprising the same as an active ingredient.

2. Description of the Related Art

Recently, the resistance problem of EGFR (epidermal growth factor receptor) targeting anticancer agents known as blockbusters has emerged, and accordingly, development of a novel anticancer agent is required.

On the other hand, nicotinamide adenine dinucleotide phosphate-dependent steroid dehydrogenase (NADP-dependent steroid dehydrogenase-like; NSDHL), which acts on the cholesterol synthesis pathway in the human body, is basically known as a sterol synthase, but recently, it has been shown to overcome the resistance to EGF (epidermal growth factor) receptor-targeting anticancer agent through its inhibition and to suppress the cancer growth through metabolic regulation, attracting attention as a new anticancer agent target (Non-Patent Reference 1, Nat Commun. 2015 Oct. 12; 6:8613). It has also been reported that nicotinamide adenine dinucleotide phosphate-dependent steroid dehydrogenase plays an important role in the metastasis of breast cancer.

In addition, when there is a congenital abnormality in the nicotinamide adenine dinucleotide phosphate-dependent steroid dehydrogenase gene, it is known that CK syndrome and CHILD (congenital hemidysplasia with ichthyosiform nevus and limb defects) syndrome occur due to the abnormal accumulation of steroid precursors by the modification of the keratinocyte outer cell membrane, and it is expected to give an important clue to the treatment of congenital hereditary diseases.

Furthermore, since nicotinamide adenine dinucleotide phosphate-dependent steroid dehydrogenase is closely related to hyperlipidemia, compounds that inhibit the function of nicotinamide adenine dinucleotide phosphate-dependent steroid dehydrogenase protein with high activity can be used in the treatment of important human diseases in the future.

SUMMARY OF THE INVENTION

It is an object of the present invention to provide a compound that effectively inhibits nicotinamide adenine dinucleotide phosphate-dependent steroid dehydrogenase (NADP-dependent steroid dehydrogenase-like; NSDHL).

It is another object of the present invention to provide a pharmaceutical composition for preventing or treating cancer comprising the compound as an active ingredient.

It is another object of the present invention to provide a pharmaceutical composition for preventing or treating hyperlipidemia comprising the compound as an active ingredient.

It is another object of the present invention to provide a health functional food composition for preventing or ameliorating cancer comprising the compound as an active ingredient.

It is another object of the present invention to provide a health functional food composition for preventing or ameliorating hyperlipidemia comprising the compound as an active ingredient.

It is another object of the present invention to provide a method of treating cancer comprising a step of administering the compound to a subject in need thereof.

It is another object of the present invention to provide a method of treating hyperlipidemia comprising a step of administering the compound to a subject in need thereof.

It is another object of the present invention to provide the above compound for use in the prevention or treatment of cancer.

It is another object of the present invention to provide the above compound for use in the prevention or treatment of hyperlipidemia.

It is another object of the present invention to provide a use of the compound for preparing a medicament for use in the prevention or treatment of cancer.

It is another object of the present invention to provide a use of the compound for preparing a medicament for use in the prevention or treatment of hyperlipidemia.

To achieve the above objects, in an aspect of the present invention, the present invention provides a compound represented by formula 1 below, a solvate thereof, a hydrate thereof, or a pharmaceutically acceptable salt thereof.

[Formula 1]

In formula 1,

R is as defined in this specification.

In another aspect of the present invention, the present invention provides a pharmaceutical composition for preventing or treating cancer comprising the above compound as an active ingredient.

In another aspect of the present invention, the present invention provides a pharmaceutical composition for preventing or treating hyperlipidemia comprising the above compound as an active ingredient.

In another aspect of the present invention, the present invention provides a health functional food composition for preventing or ameliorating cancer comprising the above compound as an active ingredient.

In another aspect of the present invention, the present invention provides a health functional food composition for preventing or ameliorating hyperlipidemia comprising the above compound as an active ingredient.

In another aspect of the present invention, the present invention provides a method of treating cancer comprising a step of administering the compound to a subject in need thereof.

In another aspect of the present invention, the present invention provides a method of treating hyperlipidemia comprising a step of administering the compound to a subject in need thereof.

In another aspect of the present invention, the present invention provides the above compound for use in the prevention or treatment of cancer.

In another aspect of the present invention, the present invention provides the above compound for use in the prevention or treatment of hyperlipidemia.

In another aspect of the present invention, the present invention provides a use of the compound for preparing a medicament for use in the prevention or treatment of cancer.

In another aspect of the present invention, the present invention provides a use of the compound for preparing a medicament for use in the prevention or treatment of hyperlipidemia.

Advantageous Effect

A nicotinamide adenine dinucleotide phosphate-dependent steroid dehydrogenase-like (NSDHL) inhibitor provided according to an aspect of the present invention can be used not only as an anticancer agent capable of overcoming resistance to FGFR-targeting anticancer agents, but also advantageously in the treatment of hyperlipidemia.

DESCRIPTION OF THE PREFERRED EMBODIMENTS

Hereinafter, the present invention is described in detail.

In an aspect of the present invention, the present invention provides a compound represented by formula 1 below, a solvate thereof, a hydrate thereof, or a pharmaceutically acceptable salt thereof.

[Formula 1]

In formula 1,
R is

A1 is —H, or nonsubstituted or substituted C6-10 aryl C1-5 straight or branched alkoxy, wherein the substituted C6-10 aryl C1-5 straight or branched alkoxy is the C6-10 aryl C1-5 straight or branched alkoxy substituted with one or more substituents selected from the group consisting of halogen (—F, —Cl, —Br, —I), nitro, nitrile and —COOH;
A2 is —H or —OH;
A3 is —H, halogen, or nonsubstituted or substituted C6-10 aryl, wherein the substituted C6-10 aryl is the aryl substituted with one or more halogens;
A4 is —H, or C1-5 straight or branched alkoxy;
B1 is —H, or nonsubstituted or substituted C6-10 aryl, wherein the substituted C6-10 aryl is the aryl substituted with one or more halogens; and
B2 is —H, or nonsubstituted or substituted C6-10 aryl, wherein the substituted C6-10 aryl is the aryl substituted with one or more halogens.
In another aspect of the present invention,
A1 is nonsubstituted or substituted benzyloxy, wherein the substituted benzyloxy is the benzyloxy substituted with one or more substituents selected from the group consisting of halogen and —COOH;
A2 is —H or —OH;
A3 is —H, halogen, or nonsubstituted or substituted phenyl, wherein the substituted phenyl is the phenyl substituted with one or more halogens;
A4 is —H or methoxy;
B1 is phenyl substituted with one halogen; and
B2 is phenyl substituted with one halogen.

In another aspect of the present invention, the compound represented by formula 1 can be selected from the group consisting of the following compounds:
(1) (Z)-4-((3-((3-(carboxymethyl)-4-oxo-2-thioxothiazolidin-5-ylidene)methyl)-4'-fluorobiphenyl-4-yloxy)methyl)benzoic acid;
(2) (Z)-2-(5-((3-(3-chlorophenyl)-1-(4-fluorophenyl)-1H-pyrazole-4-yl)methylene)-4-oxo-2-thioxothiazolidin-3-yl)acetic acid;
(3) (Z)-2-(5-(2-(benzyloxy)-6-methoxybenzylidene)-4-oxo-2-thioxothiazolidin-3-yl)acetic acid;
(4) (Z)-2-(5-(2-(2-bromobenzyloxy)-4-hydroxybenzylidene)-4-oxo-2-thioxothiazolidin-3-yl)acetic acid; and
(5) (Z)-2-(5-(5-bromo-2-(2-iodobenzyloxy)benzylidene)-4-oxo-2-thioxothiazolidin-3-yl)acetic acid.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt according to the present invention can be prepared by the conventional method known to those in the art. For example, the derivative represented by formula 1 is dissolved in an organic solvent such as methanol, ethanol, acetone, dichloromethane, and acetonitrile, to which organic acid or inorganic acid is added to induce precipitation. Then, the precipitate is filtered and dried to give the salt. Or the solvent and the excessive acid are distilled under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

In addition, the present invention includes not only the compound represented by formula 1 but also a pharmaceutically acceptable salt thereof, and a solvate, an optical isomer, or a hydrate possibly produced from the same.

In another aspect of the present invention, the present invention provides a pharmaceutical composition for preventing or treating cancer comprising the compound represented by formula 1, the solvate thereof, the hydrate thereof, or the pharmaceutically acceptable salt thereof as an active ingredient. The compound inhibits and suppresses nicotinamide adenine dinucleotide phosphate-dependent steroid dehydrogenase (NADP-dependent steroid dehydrogenase-like; NSDHL), indicating the preventive or therapeutic activity against cancer. The pharmaceutical composition can be an anticancer agent composition. The cancer can be selected from the group consisting of renal cell carcinoma, bladder cancer, liver cancer, thymus cancer, blood cancer, ovarian cancer, cervical cancer, breast cancer, colorectal cancer, stomach cancer, pancreatic cancer, colon cancer, peritoneal metastasis cancer, skin cancer, bladder cancer, prostate cancer, lung cancer, osteosarcoma, fibrous tumor and brain tumor, but not always limited thereto.

In another aspect of the present invention, the present invention provides a pharmaceutical composition for preventing or treating hyperlipidemia comprising the compound represented by formula 1, the solvate thereof, the hydrate thereof, or the pharmaceutically acceptable salt thereof as an active ingredient. The compound inhibits and suppresses nicotinamide adenine dinucleotide phosphate-dependent steroid dehydrogenase (NADP-dependent steroid dehydrogenase-like; NSDHL), indicating the preventive or therapeutic activity against hyperlipidemia.

The compound represented by formula 1 of the present invention or the pharmaceutically acceptable salt thereof can be administered orally or parenterally and be used in general forms of pharmaceutical formulation. That is, the compound or the pharmaceutically acceptable salt thereof can be prepared for oral or parenteral administration by mixing with generally used diluents or excipients such as fillers, extenders, binders, wetting agents, disintegrating agents and surfactants. Solid formulations for oral administration are tablets, pills, powders, granules and capsules. These solid formulations are prepared by mixing one or more compounds with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc.

The pharmaceutical composition comprising the compound represented by formula 1 or the pharmaceutically acceptable salt thereof as an active ingredient can be administered by parenterally and the parenteral administration includes subcutaneous injection, intravenous injection, intramuscular injection, or intrathoracic injection.

At this time, to prepare the compound represented by formula 1 or the pharmaceutically acceptable salt thereof as a formulation for parenteral administration, the compound represented by formula 1 or the pharmaceutically acceptable salt thereof is mixed with a stabilizer or a buffering agent in water to produce a solution or suspension, which is then formulated as ampoules or vials. The composition herein can be sterilized and additionally contains preservatives, stabilizers, wettable powders or emulsifiers, salts and/or buffers for the regulation of osmotic pressure, and other therapeutically useful materials, and the composition can be formulated by the conventional mixing, granulating or coating method.

The formulations for oral administration are exemplified by tablets, pills, hard/soft capsules, solutions, suspensions, emulsions, syrups, granules, elixirs, and troches, etc. These formulations can include diluents (for example, lactose, dextrose, sucrose, mannitol, sorbitol, cellulose, and/or glycine) and lubricants (for example, silica, talc, stearate and its magnesium or calcium salt, and/or polyethylene glycol) in addition to the active ingredient. Tablets can include binding agents such as magnesium aluminum silicate, starch paste, gelatin, methylcellulose, sodium carboxymethylcellulose and/or polyvinylpyrolidone, and if necessary disintegrating agents such as starch, agarose, alginic acid or its sodium salt or azeotropic mixtures and/or absorbents, coloring agents, flavours, and sweeteners can be additionally included thereto.

In another aspect of the present invention, the present invention provides a health functional food composition for preventing or ameliorating cancer comprising the compound represented by formula 1, the solvate thereof, the hydrate thereof, or the pharmaceutically acceptable salt thereof as an active ingredient.

In another aspect of the present invention, the present invention provides a health functional food composition for preventing or ameliorating hyperlipidemia comprising the compound represented by formula 1, the solvate thereof, the hydrate thereof, or the pharmaceutically acceptable salt thereof as an active ingredient.

The compound represented by formula 1 of the present invention can be used as a food additive. In that case, the compound represented by formula 1 of the present invention can be added as it is or as mixed with other food components according to the conventional method. The mixing ratio of active ingredients can be regulated according to the purpose of use (prevention or amelioration). In general, the compound of the present invention is preferably added to food or beverages by 0.1~ 90 weight part for the total weight of the food. However, if long term administration is required for health and hygiene or regulating health condition, the content can be lower than the above but higher content can be accepted as well since the compound of the present invention has been proved to be very safe.

In addition, the health beverage composition of the present invention can additionally include various flavors or natural carbohydrates, etc, like other beverages. The natural carbohydrates above can be one of monosaccharides such as glucose and fructose; disaccharides such as maltose and sucrose; polysaccharides such as dextrin and cyclodextrin, and sugar alcohols such as xilytole, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. The content of the natural carbohydrate is preferably 1~20 g and more preferably 5~12 g in 100 g of the composition of the invention.

In addition to the ingredients mentioned above, the compound represented by formula 1 of the present invention can include in variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The compound represented by formula 1 of the present invention can also include natural fruit juice, fruit beverages and fruit flesh addable to vegetable beverages.

In another aspect of the present invention, the present invention provides a method of treating cancer comprising a step of administering the compound to a subject in need thereof. In another aspect of the present invention, the present invention provides a method of treating hyperlipidemia comprising a step of administering the compound to a subject in need thereof.

In another aspect of the present invention, the present invention provides the above compound for use in the prevention or treatment of cancer. In another aspect of the present invention, the present invention provides the above compound for use in the prevention or treatment of hyperlipidemia.

In another aspect of the present invention, the present invention provides a use of the compound for preparing a medicament for use in the prevention or treatment of cancer. In another aspect of the present invention, the present invention provides a use of the compound for preparing a medicament for use in the prevention or treatment of hyperlipidemia.

A nicotinamide adenine dinucleotide phosphate-dependent steroid dehydrogenase-like (NSDHL) inhibitor provided according to an aspect of the present invention can be used not only as an anticancer agent capable of overcoming resistance to EGFR-targeting anticancer agents, but also advantageously in the treatment of hyperlipidemia, which is supported by Examples and Experimental Examples described later.

Hereinafter, the present invention will be described in detail by the following examples and experimental examples.

However, the following examples and experimental examples are only for illustrating the present invention, and the contents of the present invention are not limited thereto.

<Example 1> (Z)-4-((3-((3-(carboxymethyl)-4-oxo-2-thioxothiazolidin-5-ylidene)methyl)-4'-fluorobiphenyl-4-yloxy)methyl)benzoic acid

A title compound was obtained from Korea Chemical Bank. (ID: 461974)

<Example 2> (Z)-2-(5-((3-(3-chlorophenyl)-1-(4-fluorophenyl)-1H-pyrazole-4-yl)methylene)-4-oxo-2-thioxothiazolidin-3-yl)acetic acid

A title compound was obtained from Korea Chemical Bank. (ID: 179862)

<Example 3> (Z)-2-(5-(2-(benzyloxy)-6-methoxy-benzylidene)-4-oxo-2-thioxothiazolidin-3-yl)acetic acid

A title compound was obtained from Korea Chemical Bank. (ID: 118448)

<Example 4> (Z)-2-(5-(2-(2-bromobenzyloxy)-4-hydroxybenzylidene)-4-oxo-2-thioxothiazolidin-3-yl)acetic acid A title compound was obtained from Korea Chemical Bank. (ID: 129671)

<Example 5> (Z)-2-(5-(5-bromo-2-(2-iodobenzyloxy)benzylidene)-4-oxo-2-thioxothiazolidin-3-yl) acetic acid A title compound was obtained from Korea Chemical Bank. (ID: 118459)

The chemical formulas of the compounds prepared in Examples 1 to 5 are summarized and shown in Table 1 below.

TABLE 1

| Example | Structure |
| --- | --- |
| 1 | |
| 2 | |
| 3 | |
| 4 | |
| 5 | |

<Experimental Example 1> Evaluation of Nicotinamide Adenine Dinucleotide Phosphate-Dependent Steroid Dehydrogenase (NSDHL) Inhibitory Activity Evaluation In order to evaluate the nicotinamide adenine dinucleotide phosphate-dependent steroid dehydrogenase (NSDHL) inhibitory activity of the compound provided in one aspect of the present invention, the following experiment was performed.

<1-1> Expression of NSDHL

Human-derived nicotinamide adenine dinucleotide phosphate-dependent steroid dehydrogenase (NADP-dependent steroid dehydrogenase-like; NSDHL) was expressed in large quantities in E. coli. The NSDHL gene was inserted into pET21a plasmid, which was cloned into E. coli C41 (DE3). After culturing E. coli in Luria Broth medium at 37° C., IPTG was added thereto at the time when $OD_{600}$ was about 0.7 to express NSDHL, followed by culture at 37° C. for 4 hours.

<1-2> Purification and Separation of NSDHL Protein

The cultured E. coli was centrifuged, and the cells were stored at −80° C. The cells were crushed by sonification, which was first purified using IMAC (Immobilized metallo-affinity chromatography), and then finally purified using SEC (Size exclusion chromatography). The composition of the buffer solution for storing NSDHL was as follows: 40 mM HEPES (pH 8.0), 150 mM NaCl, and 0.5 mM TCEP.

Figure 1:
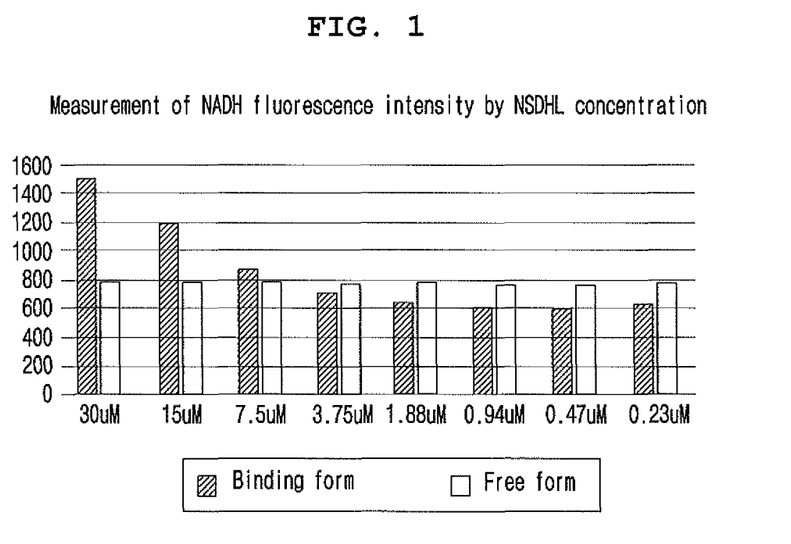
FIG. 1 is a graph showing the results of measuring the fluorescence intensity of NADH according to the concentration of NSDHL.

<1-3> $IC_{50}$ Measurement and Inhibitor Detection Using Fluorescence Intensity Amplification that Appears when Dehydrogenase Binds to NADH When dehydrogenase binds to NADH, fluorescence intensity is amplified compared to NADH alone. In other words, if the dehydrogenase, NSDHL, is treated with an inhibitor in a state in which it is bound to NADH, the fluorescence intensity will be reduced because NADH is released. The results of measuring the fluorescence intensity of NADH according to the concentration of NSDHL are shown in FIG. 1. FIG. 1 is a graph showing the results of measuring the fluorescence intensity of NADH according to the concentration of NSDHL. As shown in FIG. 1, it was confirmed that the fluorescence intensity was amplified when NSDHL was reacted with NADH by concentration.

Figure 2:
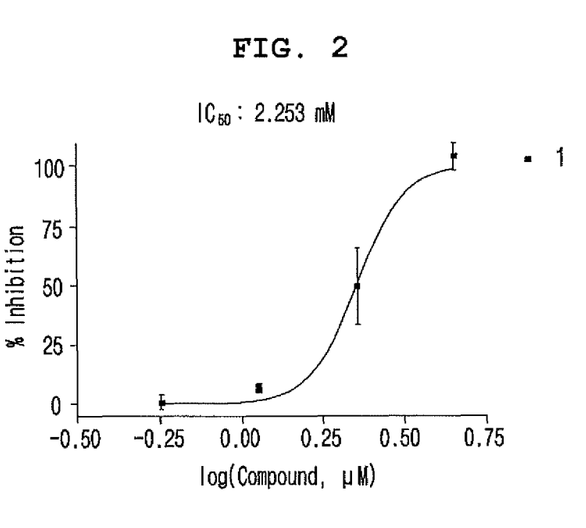
FIG. 2 is a graph showing the results of an experiment for inhibiting NSDHL and NADH conjugate using NAD+.

In addition, it was also confirmed in FIG. 2 that an experiment for inhibiting was possible using NAD+, which is an oxidized form of NADH, but is not measured in the fluorescence measurement range of NADH. FIG. 2 is a graph showing the results of an experiment for inhibiting NSDHL and NADH conjugate using NAD+.

<1-4> Screening of Lead Compound

An activity assay was performed using a 96-well plate, and an experiment was performed after adding an inhibitor to each well at the final concentrations of 200 µM≤1 µM. Particularly, 50 µl of 16 µM NSDHL, 50 mM HEPES, 20% glycerol were added to each well, and then 50 ul of 50 µM NADH was added to each well, followed by reaction at room temperature for 10 minutes. The fluorescence level of each well was measured using SpectraMax M5 (Molecular Devices) equipment (Ex: 340 nm, Em: 460 nm). The values were corrected by separately measuring the absorbance of the compound and the buffer solution, and the degree of inhibition of each compound against NSDHL was measured based on the NADH fluorescence at the same concentration without binding. $IC_{50}$ (inhibitory concentration at 50%) was calculated using GraphPad Prism software. The results are shown in Table 2 below.

TABLE 2

| Example | $IC_{50}$ (µM) |
|---|---|
| 1 | 10.43 |
| 2 | 12.78 |
| 3 | 19.85 |
| 4 | 17.78 |
| 5 | 27.13 |

As shown in Table 2, it was confirmed that the compounds of Examples 1 to 5 effectively inhibited dehydrogenase.

<Manufacturing Example 1> Preparation of Pharmaceutical Formulations

<1-1> Preparation of Powders
Compound represented by formula 1 500 mg
Lactose 100 mg
Talc 10 mg
Powders were prepared by mixing all the above components, which were filled in airtight packs according to the conventional method for preparing powders.

<1-2> Preparation of Tablets
Compound represented by formula 1 500 mg
Corn starch 100 mg
Lactose 100 mg
Magnesium stearate 2 mg
Tablets were prepared by mixing all the above components by the conventional method for preparing tablets.

<1-3> Preparation of Capsules
Compound represented by formula 1 500 mg
Corn starch 100 mg
Lactose 100 mg
Magnesium stearate 2 mg
Capsules were prepared by mixing all the above components, which were filled in gelatin capsules according to the conventional method for preparing capsules.

<1-4> Preparation of injectable solutions
Compound represented by formula 1 500 mg
Sterilized distilled water proper amount
pH regulator proper amount
Injectable solutions were prepared with the above ingredients per ampoule (2 mi) according to the conventional method for preparing injectable solutions.

<1-5> Preparation of Liquid Formulations
Compound represented by formula 1 500 mg
Isomerized sugar 10 g
Mannitol 5 g
Purified water proper amount
All the above components were dissolved in purified water. After adding lemon flavor, total volume was adjusted to be 100 me by adding purified water. Liquid formulations were prepared by putting the mixture into brown bottles and sterilizing thereof by the conventional method for preparing liquid formulations.

INDUSTRIAL APPLICABILITY

A nicotinamide adenine dinucleotide phosphate-dependent steroid dehydrogenase-like (NSDHL) inhibitor provided according to an aspect of the present invention can be used not only as an anticancer agent capable of overcoming resistance to EGFR-targeting anticancer agents, but also advantageously in the treatment of hyperlipidemia.

What is claimed is:

1. A compound, a solvate thereof, a hydrate thereof, or a pharmaceutically acceptable salt thereof, wherein the compound is
- (Z)-4-((3-((3-(carboxymethyl)-4-oxo-2-thioxothiazolidin-5-ylidene)methyl)-4'-fluorobiphenyl-4-yloxy)methyl)benzoic acid or
- (Z)-2-(5-(2-(2-bromobenzyloxy)-4-hydroxybenzylidene)-4-oxo-2-thioxothiazolidin-3-yl)acetic acid.

2. A method of treating hyperlipidemia comprising the step of administering a compound, a solvate thereof, a hydrate thereof, or a pharmaceutically acceptable salt thereof to a subject in need, wherein the compound is (Z)-4-((3-((3-(carboxymethyl)-4-oxo-2-thioxothiazolidin-5-ylidene)methyl)-4'-fluorobiphenyl-4-yloxy)methyl)benzoic acid or (Z)-2-(5-(2-(2-bromobenzyloxy)-4-hydroxybenzylidene)-4-oxo-2-thioxothiazolidin-3-yl)acetic acid.

* * * * *